(12) United States Patent
Nöcker et al.

(10) Patent No.: US 12,350,360 B2
(45) Date of Patent: *Jul. 8, 2025

(54) COSMETIC PRODUCT FOR DYEING KERATIN FIBERS

(71) Applicant: KAO CORPORATION, Tokyo (JP)

(72) Inventors: Bernd Nöcker, Darmstadt (DE); Qi Uellner, Darmstadt (DE); Steven Breakspear, Darmstadt (DE)

(73) Assignee: KAO CORPORATION, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/554,833

(22) PCT Filed: Apr. 26, 2022

(86) PCT No.: PCT/EP2022/061027
§ 371 (c)(1),
(2) Date: Oct. 11, 2023

(87) PCT Pub. No.: WO2022/229168
PCT Pub. Date: Nov. 3, 2022

(65) Prior Publication Data
US 2024/0197606 A1    Jun. 20, 2024

(30) Foreign Application Priority Data

Apr. 26, 2021    (EP) .................................. 21170400

(51) Int. Cl.
| | | |
|---|---|---|
| *A61Q 5/10* | (2006.01) | |
| *A61K 8/22* | (2006.01) | |
| *A61K 8/41* | (2006.01) | |
| *A61K 8/46* | (2006.01) | |
| *A61K 8/49* | (2006.01) | |
| *A61Q 5/06* | (2006.01) | |

(52) U.S. Cl.
CPC .............. *A61K 8/4953* (2013.01); *A61K 8/22* (2013.01); *A61K 8/41* (2013.01); *A61K 8/466* (2013.01); *A61K 8/4946* (2013.01); *A61Q 5/065* (2013.01); *A61K 2800/4322* (2013.01); *A61K 2800/882* (2013.01)

(58) Field of Classification Search
CPC .......... A61K 8/4953; A61K 8/22; A61K 8/41; A61K 8/466; A61K 8/4946; A61K 2800/4322; A61K 2800/882; A61K 2800/88; A61K 8/347; A61Q 5/065; A61Q 5/10
USPC ............................................................ 8/405
See application file for complete search history.

(56) References Cited

U.S. PATENT DOCUMENTS

| | | | | | |
|---|---|---|---|---|---|
| 4,668,236 A | * | 5/1987 | Grollier | ................. | A61K 8/418 |
| | | | | | 8/405 |
| 4,931,066 A | * | 6/1990 | Grollier | ................. | A61K 8/418 |
| | | | | | 8/408 |
| 10,052,273 B2 | * | 8/2018 | Lalleman | ............... | A61K 8/498 |
| 10,485,744 B2 | * | 11/2019 | Wahler | ..................... | A61K 8/41 |
| 2010/0154144 A1 | | 6/2010 | Guerin et al. | | |
| 2010/0158844 A1 | | 6/2010 | Braida-Valerio et al. | | |
| 2017/0258695 A1 | * | 9/2017 | Consoli | ..................... | A61K 8/55 |
| 2017/0326048 A1 | * | 11/2017 | Wahler | ..................... | A61K 8/19 |

FOREIGN PATENT DOCUMENTS

| | | | |
|---|---|---|---|
| DE | 10 2006 061 830 A1 | 6/2008 | |
| DE | 10 2007 041 493 A1 | 3/2009 | |
| EP | 1 153 598 A2 | 11/2001 | |
| EP | 2 196 182 A2 | 6/2010 | |
| EP | 2 198 923 A2 | 6/2010 | |
| WO | WO 2009/053180 A1 | 4/2009 | |
| WO | WO 2018115393 A1 * | 6/2018 | ............... A61Q 5/10 |

OTHER PUBLICATIONS

STIC Search Report dated Nov. 12, 2024.*
International Search Report and Written Opinion issued Aug. 17, 2022 in PCT/EP2022/061027 filed on Apr. 26, 2022, 13 pages.
European Search Report issued Nov. 9, 2021 in European Application 21170400.2 filed on Apr. 26, 2021, 10 pages.
Mintel #6713099, Caffeine Shampoo, http://www.gnpd.com, Jul. 2019, 2 pages.

* cited by examiner

*Primary Examiner* — Eisa B Elhilo
(74) *Attorney, Agent, or Firm* — Oblon, McClelland, Maier & Neustadt, L.L.P.

(57) ABSTRACT

A cosmetic product, including a composition A containing one or more alkalizing agents and one or more direct dyes, and an aqueous composition B having a pH in a range of 1 to 6. The aqueous composition B contains hydrogen peroxide, and one or more compounds selected from the following groups:

1)

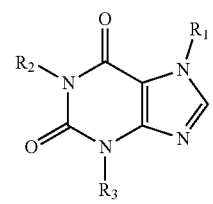

where $R_1$, $R_2$, and $R_3$ are independently selected from H and $CH_3$, 2) one or more orthodiphenols or a derivative or salt thereof, and 3) one or more imidazolidin-2,4-diones or a derivative or salt thereof.

20 Claims, No Drawings

COSMETIC PRODUCT FOR DYEING KERATIN FIBERS

CROSS REFERENCE TO RELATED APPLICATIONS

This application is a National Stage entry under 35 U.S.C. § 371 of PCT/EP2022/061027, filed on Apr. 26, 2022, and claims priority to European Patent Application No. 21170400.2, filed on Apr. 26, 2021. The entire contents of both are incorporated herein by reference.

FIELD OF THE INVENTION

The present invention relates to a cosmetic product for dyeing of keratin fibers comprising. Furthermore, a dyeing method and use are disclosed.

BACKGROUND OF THE INVENTION

Aqueous, hydrogen peroxide-containing compositions are well known in the art. These compositions are essential components in many industrial and artisanal processes. For example, bleaching or dyeing of solid substrates require the presence of oxidizing compositions. In particular paper, wool, and cosmetic industry rely on the performance of these compositions.

However, a common problem of such compositions is that the hydrogen peroxide tends to undergo a decomposition process during storage whereby the available active oxygen in the composition decreases over time. This decomposition process particularly represents a problem for bleaching, dyeing, and permanent waving processes. It is essential for the user of hydrogen-peroxide compositions that they have a long shelf life in order to retain their original performance.

The self-decomposition process of hydrogen peroxide increases with temperature. Thus, decomposition progresses faster in warm climate countries or under less than ideal storage conditions at the user's facilities. As a result, the user is confronted with lower performance in coloring, bleaching, or permanent waving processes compared to results obtained a couple of months ago with compositions having shorter storage times.

The prior art has not sufficiently solved this problem.

For example, EP2198923 focuses on formulation stability, but not on chemical stability of aqueous oxidizing composition.

Xanthine and its derivatives are well-known ingredients in pharmaceutical and food industry. Moreover, cleansing compositions comprising caffeine are well-known (e.g. Mintel #6713099).

WO2009/053180 discloses aqueous oxidizing compositions comprising 5% by weight or less of hydrogen peroxide and purine derivatives, in particular caffeine. It was found that purine derivatives reduce damage to keratin fibers.

Despite the attempts of the prior art, there still is a need to improve the stability of hydrogen peroxide in combination with the dyeing performance of direct dyes.

SUMMARY OF THE INVENTION

The first object of the present invention is a cosmetic product for dyeing of keratin fibers, preferably for dyeing of human keratin fibers, more preferably for dyeing of human hair, comprising:
  a composition A comprising one or more alkalizing agent(s) and one or more direct dye(s),
  an aqueous composition B having a pH in the range of 1 to 6 and comprising:

1)

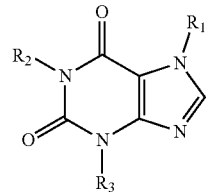

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s).

The second object of the present invention is a kit-of-parts comprising the compositions A and B as defined above and one more composition selected from:
  a bleaching powder composition C comprising one or more persalt(s) and/or peroxy salt(s) and one or more alkalizing agent(s),
  an aqueous lightening composition D comprising one or more alkalizing agent(s) and having a pH in the range of 7 to 12,
  an aqueous dyeing composition E having a pH in the range of 7 to 12 and comprising one or more dye selected from oxidative dye precursor(s), oxidative dye coupler(s), and/or direct dye(s), and/or their salt(s), and/or their mixtures.

The third object of the present invention is a method for dyeing of keratin fibers, preferably human keratin fibers, more preferably human hair, comprising the steps of:
  i) providing compositions A and B as defined above,
  ii) mixing the compositions to yield a ready-to-use composition having a pH in the range of 7 to 12,
  iii) applying the ready-to-use composition onto keratin fibers and leaving it for a time period of 1 to 60 min,
  iv) rinsing off the keratin fibers and optionally shampooing the keratin fibers.

The fourth object of the present invention is a use of one or more compound(s) selected from:

1)

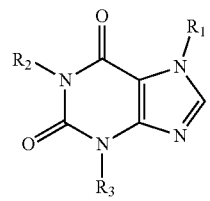

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s), for improving color intensity and/or wash fastness of direct dyes on keratin fibers, preferably on human keratin fibers, more preferably on human hair.

DETAILED DESCRIPTION OF THE INVENTION

Inventors of the present invention have unexpectedly found out that a cosmetic product according to claim 1 increased chemical and physical storage stability of aqueous oxidizing compositions comprising hydrogen peroxide at room and elevated temperature alike. Moreover, the dyeing results of the composition were found to be more intense and had improved wash fastness. Thus, the performance of the composition was unexpectedly found to be more consistent over time.

Cosmetic Product

The present invention is directed to a cosmetic product for dyeing of keratin fibers, preferably for dyeing of human keratin fibers, more preferably for dyeing of human hair, comprising:
a composition A comprising one or more alkalizing agent(s) and one or more direct dye(s),
an aqueous composition B having a pH in the range of 1 to 6 and comprising:

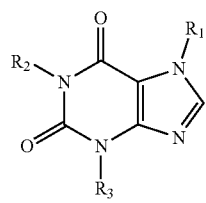

1)

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s).

Composition A

The present invention is in part directed to a composition A comprising one or more alkalizing agent(s) and one or more direct dye(s).

Composition A of the present invention comprises one or more alkalizing agent(s).

It is preferred from the viewpoint of providing alkalinity and cosmetic safety that one or more alkalizing agent(s) is/are one or more organic alkalizing agent(s) and/or its/their salt(s), and/or ammonia and/or its salt(s).

Preferably, one or more organic alkalizing agent(s) are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane, and/or its/their salt(s), and/or their mixtures, from the viewpoint of providing alkalinity and cosmetic safety as well as their low odor.

The most preferred alkalizing agent(s) it is selected from monoethanolamine, 2-amino-2-methylpropanol, tris-(hydroxymethyl)-aminomethane, and/or its/their salt(s), ammonia and or its salt(s), and/or their mixtures, from the viewpoint of providing alkalinity and cosmetic safety.

In one aspect of the present invention, it may be suitable from the viewpoint of storage stability that one or more alkalizing agent(s) is one or more inorganic alkalizing agent(s), preferably selected from metasilicates, carbonates, and/or bicarbonates, and/or their alkali or earth alkali salts, and/or their mixtures, preferably it is sodium metasilicate.

It is preferred from the viewpoint of providing alkalinity that the total concentration of alkalizing agent(s), preferably the total concentration of one or more alkanolamine(s) and/or its/their salt(s) and/or ammonia and/or its salt(s), is 0.1% by weight or more, more preferably 0.25% by weight or more, further more preferably 0.5% by weight or more, calculated to the total weight of composition A.

It is preferred from the viewpoint of providing alkalinity, hair damage, and odor that the total concentration of alkalizing agent(s), preferably the total concentration of one or more alkanolamine(s) and/or its/their salt(s) and/or ammonia and/or its salt(s), is 40% by weight or less, more preferably 30% by weight or less, further more preferably 25% by weight or less, calculated to the total weight of composition A.

For attaining the above-mentioned effects, it is preferred that the total concentration of alkalizing agent(s), preferably the total concentration of one or more alkanolamine(s) and/or its/their salt(s) and/or ammonia and/or its salt(s), is in the range of 0.1% to 40% by weight, preferably in the range of 0.25% to 30% by weight, more preferably in the range of 0.5% to 25% by weight, calculated to the total weight of composition A.

Composition A of the present invention comprises one or more direct dye(s).

In principle, all direct dyes are suitable for the purpose of the present inventions. In particular, anionic, cationic, or neutral direct dyes are suitable.

Suitable anionic direct dyes are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16.

Suitable cationic dyes are in principle those available on the market for cosmetic hair colouring applications. For this purpose, special reference is made to the PCT application WO 95/15144 of Ciba-Geigy AG. Some examples to those are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124.

Suitable neutral dyes including nitro dyes are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-amino-6-chloro-4-nitrophenol, picramic acid, 1-Hydroxy-2-amino-3-nitrobenzol and 2-hydroxyethylpicramic acid.

It is preferred from the viewpoint of dyeing intensity and wash fastness, that one or more direct dye(s) is selected from HC Blue 18, HC Red 18, HC Yellow 16, Disperse Black 9, Acid Yellow 1, 2-amino-6-chloro-4-nitrophenol, and/or their salt(s), and/or their mixtures.

It is preferred from the viewpoint of color intensity that the total concentration of direct dyes is 0.001% by weight or more, further preferably 0.005% by weight or more, still more preferably 0.01% by weight or more, calculated to the total weight of composition A.

It is preferred from the viewpoint of color intensity and economic reasons that the total concentration of direct dyes is 10% by weight or less, further preferably 5% by weight or less, still more preferably 3% by weight or less, still further more preferably 1.5% by weight or less, still further more preferably 1% by weight or less, calculated to the total weight of composition A.

For attaining the above-mentioned effects, it is preferred that the total concentration of direct dyes is in the range of 0.001% to 10% by weight, preferably in the range of 0.005% to 5% by weight, more preferably in the range of 0.01% to 3% by weight, still further more preferably in the range of 0.01% to 1.5% by weight, still further more preferably in the range of 0.01% to 1% by weight, calculated to the total weight of composition A.

Forms of Composition A

The composition A of the present invention may be available in various cosmetic forms such as liquid composition—aqueous or non-aqueous—or powder composition.

Aqueous Composition

In one aspect of the present invention, composition A is an aqueous composition.

The term 'aqueous' denotes a composition that comprises a majority of water, i.e., composition A preferably comprises water at 50% by weight or more, further more preferably at 60% by weight or more, still more preferably at 70% by weight or more, still further more preferably at 80% by weight or more, calculated to the total weight of composition A, from the viewpoint of achieving a cosmetically acceptable composition.

It is further preferred from the viewpoint of dyeing intensity that composition A comprises water at 98% by weight or less, more preferably at 95% by weight or less, further more preferably at 92% by weight or less, calculated to the total weight of composition A.

For achieving the above-mentioned effects, it is preferred that the total concentration of water in composition A is in the range of 50% to 98% by weight, more preferably in the range of 60% to 95% by weight, further more preferably in the range of 70% to 92% by weight, still more preferably in the range of 80% to 92% by weight, calculated to the total weight of composition A.

It is preferred from the viewpoint of dyeing performance that the pH of composition A is 7 or more, more preferably the pH is 7.5 or more, further more preferably the pH is 8 or more, still further more preferably the pH is 9 or more.

It is preferred from the viewpoint of hair damage and dyeing performance that the pH of composition A is 12 or less, more preferably the pH is 11 or less, still more preferably the pH is 10.5 or less.

For attaining the above mentioned effects, it is preferred that composition A has a pH in the range of 7 to 12, preferably in the range of 7.5 to 11, more preferably in the range of 8 to 10.5, further more preferably in the range of 9 to 10.5.

Thus, the present disclosure is also directed to a cosmetic product for dyeing of keratin fibers, preferably for dyeing of human keratin fibers, more preferably for dyeing of human hair, comprising:

a composition A comprising one or more alkalizing agent(s) and one or more direct dye(s),
an aqueous composition B having a pH in the range of 1 to 6 and comprising:
a) hydrogen peroxide, and
b) one or more compound(s) selected from the following groups:

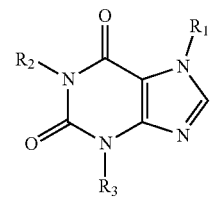

1)

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s),
wherein composition A is an aqueous composition comprising 50% by weight of water or more and has a pH in the range of 7 to 12.

Optionally, composition A may further comprise one or more organic solvent(s), as also defined for the composition comprising less than 1% by weight of water.

Suitably, these solvents include benzyl alcohol, ethanol, phenoxyethanol. Suitable concentration range from 1% by weight to 10% by weight, calculated to the total weight of composition A.

Liquid Composition Comprising Less than 1% by Weight of Water

In another aspect of the present invention, composition A is a liquid composition at 25° C. and atmospheric pressure comprising one or more organic solvent(s) as compound(s) and less than 1% by weight of water, calculated to the total weight of composition A. Preferably, the composition is anhydrous, from the viewpoint of dye stability.

The term 'liquid' denotes a physical state at 25° C. and atmospheric pressure, i.e., the dyeing composition is liquid at room temperature.

The term 'anhydrous' denotes a composition, which is free of added water. This does not exclude the presence of residual moisture from air or crystal water bound to ingredients.

For this aspect of the present invention, composition A may comprise one or more organic solvent(s).

The organic solvent(s) may be selected to dissolve the alkalizing agents and dyes.

Preferred solvents are mono-, di-, and trivalent alcohols and/or their mixtures.

Preferred mono-, di-, and trivalent alcohols from the viewpoint of cosmetic safety and dissolution capacity are ethanol, n-propanol, isopropanol, propylene glycol, ethylene glycol, benzyl alcohol, phenoxyethanol, and glycerol, and/or their mixtures.

It is further preferred from the viewpoint of solution stability that the total concentration of organic solvents is 75% by weight or more, more preferably 80% by weight or more, further more preferably 85% by weight or more, calculated to the total weight of composition A.

It is further preferred from the viewpoint of dyeing intensity that the total concentration of organic solvents is 98% by weight or less, more preferably 95% by weight or less, further more preferably 92% by weight or less, calculated to the total weight of composition A.

For attaining the above-mentioned effects, it is preferred that the total concentration of organic solvents is in the range of 75% to 98% by weight, more preferably 80% to 95% by weight, further more preferably in the range of 85% to 92% by weight, calculated to the total weight of composition A.

Thus, the present disclosure is also directed to a cosmetic product for dyeing of keratin fibers, preferably for dyeing of human keratin fibers, more preferably for dyeing of human hair, comprising:
    a composition A comprising one or more alkalizing agent(s) and one or more direct dye(s),
    an aqueous composition B having a pH in the range of 1 to 6 and comprising:
a) hydrogen peroxide, and
b) one or more compound(s) selected from the following groups:

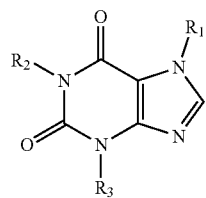

1)

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s),
wherein composition A is a liquid composition at 25° C. and atmospheric pressure and comprises one or more organic solvent(s) and less than 1% by weight of water, preferably it is anhydrous.

Powder Composition

In one aspect of the present invention, composition A may be a powder composition.

The term 'powder' denotes a solid composition at 25° C. and atmospheric pressure.

The term relates to freely flowing powders as well as compressed powders such as tablets. The powder composition may also comprise water as long as its nature of the solid state at 25° C. is unchanged. Depending on the type of powder, a water content of 10% by weight or less, calculated to the total weight of composition A, may be acceptable. This does not exclude the presence of residual moisture from air or crystal water bound to ingredients. Preferably, composition A is an anhydrous powder composition, from the viewpoint of stability.

It is preferred from the viewpoint of composition stability and convenience of use that composition A comprises one or more pulverulent excipient.

The term 'excipient' denotes a compound, which may act as filling material and dispersant for the other compounds of composition A and do not react with the dyes and the alkalizing agent, and, thus, confer the powder a high degree of storage stability over an extended period of time.

Composition A of the present invention may comprise an organic and/or an inorganic pulverulent excipient in which the alkalizing agent and direct dyes are dispersed.

Suitable organic and/or an inorganic pulverulent excipients are, for example, diatomaceous earth, kaolin, bentonite, starch especially corn, tapioca, rice, wheat and potato, nylon powder, montmorillonit, gypsum, sawdust and perlite.

The total concentration of organic and/or an inorganic pulverulent excipient preferably is 50% by weight or more, more preferably 55% by weight or more, further more preferably 60% by weight or more, still further more preferably 65% by weight or more, even further more preferably 70% by weight or more, even more preferably 75% by weight or more, calculated to the total weight of composition A, from the viewpoint of achieving good dispersability of the direct dyes in the powder and quick dissolution of the powder.

The total concentration of organic and/or an inorganic pulverulent excipient preferably is 98% by weight or less, more preferably 95% by weight or less, further more preferably 90% by weight or less, calculated to the total weight of composition A, from the viewpoint of achieving good dispersability of the direct dyes in the powder and formulation freedom.

For attaining the above mentioned effects, the total concentration of organic and/or an inorganic pulverulent excipient preferably is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of composition A.

Thus, the present disclosure is also directed to a cosmetic product for dyeing of keratin fibers, preferably for dyeing of human keratin fibers, more preferably for dyeing of human hair, comprising:
    a composition A comprising one or more alkalizing agent(s) and one or more direct dye(s),
    an aqueous composition B having a pH in the range of 1 to 6 and comprising:

a) hydrogen peroxide, and
b) one or more compound(s) selected from the following groups:

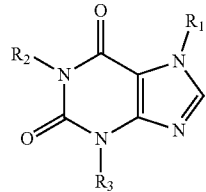

wherein $R_1$, $R_2$, and $R_3$ are independently selected from H and $CH_3$, and/or their mixtures, 2) one or more orthodiphenol(s) and/or their derivatives, and/or their mixtures, and/or their salt(s), 3) one or more imidazolidin-2,4-dione(s) and/or their derivatives, and/or their mixtures, and/or their salt(s), wherein composition A is a powder composition and comprises one or more pulverulent excipients.

In one aspect of the present invention, composition A is a bleaching powder composition and comprises one or more bleaching compounds, as detailed below for the bleaching powder composition D.

Thus, the present disclosure is also directed to a cosmetic product for dyeing of keratin fibers, preferably for dyeing of human keratin fibers, more preferably for dyeing of human hair, comprising:

a composition A comprising one or more alkalizing agent(s) and one or more direct dye(s), an aqueous composition B having a pH in the range of 1 to 6 and comprising:
a) hydrogen peroxide, and
b) one or more compound(s) selected from the following groups:

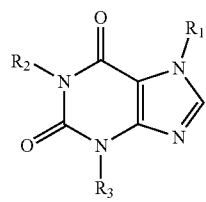

wherein $R_1$, $R_2$, and $R_3$ are independently selected from H and $CH_3$, and/or their mixtures, 2) one or more orthodiphenol(s) and/or their derivatives, and/or their mixtures, and/or their salt(s), 3) one or more imidazolidin-2,4-dione(s) and/or their derivatives, and/or their mixtures, and/or their salt(s), wherein composition A is a bleaching powder composition and comprises one or more bleaching compound(s).

Aqueous Composition B

The aqueous composition B of the present invention has a pH in the range of 1 to 6 and comprises:
a) hydrogen peroxide, and
b) one or more compound(s) selected from the following groups:

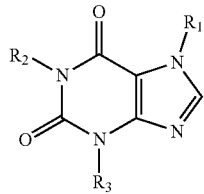

wherein $R_1$, $R_2$, and $R_3$ are independently selected from H and $CH_3$, and/or their mixtures, 2) one or more orthodiphenol(s) and/or their derivatives, and/or their mixtures, and/or their salt(s), 3) one or more imidazolidin-2,4-dione(s) and/or their derivatives, and/or their mixtures, and/or their salt(s).

It is preferred from the viewpoint of storage stability and safety of the composition that the pH of composition B is 1.25 or more, more preferably 1.5 or more, further more preferably 2 or more.

It is preferred from the viewpoint of storage stability of the composition that the pH of composition B is 5 or less, more preferably 4 or less, further more preferably 3 or less.

For attaining the above-mentioned effects, it is preferred that the pH of composition B is in the range of 1.25 to 5, more preferably in the range of 1.5 to 4, further more preferably in the range of 2 to 3.

It is further preferred from the viewpoint of product performance that the concentration of the compound according to a) is 0.1% by weight or more, more preferably 0.25% by weight or more, further more preferably 1% by weight or more, calculated to the total weight of composition B.

It is further preferred from the viewpoint of product performance and user safety that the concentration of the compound according to a) is 20% by weight or less, more preferably 15% by weight or less, further more preferably 12% by weight or less, calculated to the total weight of composition B.

For attaining the above-mentioned effects, it is preferred that the concentration of the compound according to a) is in the range of more than 0.1% to 20% by weight, more preferably in the range of 0.25% to 15% by weight, further more preferably in the range of 1% to 12% by weight, calculated to the total weight of composition B.

Composition B comprises one or more compound(s) selected from the following as compound(s) according to group b1):

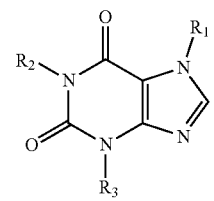

wherein $R_1$, $R_2$, and $R_3$ are independently selected from H and $CH_3$, and/or their mixtures. These compounds are xanthine and its derivatives.

Suitable xanthine and/or xanthine derivatives according to the structure of compound b1) are Xanthine with $R_1=R_2=R_3=H$,
Theobromine with $R_1=R_3=CH_3$ and $R_2=H$,
Theophylline with $R_2=R_3=CH_3$ and $R_1=H$, and Caffeine with $R_1=R_2=R_3=CH_3$.

Mixtures of the above are suitable as well.

It is preferred from the economic viewpoint that at least one or more compound(s) according to group b1) is/are caffeine and/or theobromine, and/or their mixtures, preferably it is caffeine.

It is preferred from the viewpoint of commercial availability that that one or more compound(s) according to group b2) of composition B is selected from Flavonols,
Anthocyanidines,
Anthocyanines or anthocyanes,
Orthohydroxybenzoates,
Flavones,
Hydroxystilbenes,
3,4-dihydroxyphenylalanine and its derivatives,
2,3-dihydroxyphenylalanine and its derivatives,
4,5-dihydroxyphenylalanine and its derivatives,
Dihydroxycinnamates,
Orthopolyhydroxycoumarines,
Orhtopolyhydroxyisocoumarines,
Orthopolyhydroxycoumarones,
Orthopolyhydroxyisocoumarones,
Orhtopolyhydroxychalcones,
Orhtopolyhydroxychromones,
Orhtopolyhydroxyquinones,
Orhtohydroxyxanthones,
1,2-dihyroxybenzenes and its derivatives,
1,2,4-trihydroxybenzenes and its derivatives,
1,2,3-trihydroxybenzenes and its derivatives,
2,4,5-trihydroxybenzenes and its derivatives,
Proanthocyanidines,
Proanthocyanines,
Tannic acid,
Ellagic acid,
one or more compound(s) according the following general structure:

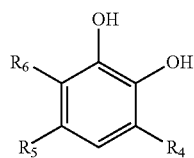

wherein $R_4$, $R_5$, and $R_6$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl,
and/or their salt(s), and/or their mixture(s).

It is preferred from the viewpoint of commercial availability that one or more compound(s) according to group b2) of composition B is selected from the following general structure:

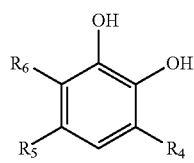

wherein $R_4$, $R_5$, and $R_6$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.

It is preferred from the viewpoint of dyeing intensity that for group b2) $R_4$ is selected from H, OH, halogen, $C_1$-$C_{12}$ linear or branched alkyl or alkenyl, O—X, $NO_2$, COOH, $SO_3H$, aryl, heteroaryl, with X being $C_1$-$C_{12}$ linear or branched alkyl, and $R_5$, and $R_6$ are independently selected from $C_1$-$C_{12}$ linear or branched alkyl or alkenyl, O—X, $NO_2$, COOH, $SO_3H$, and/or their salt(s), and/or their mixtures, with X being $C_1$-$C_{12}$ linear or branched alkyl.

Preferably, at least one compound according to group b2) is selected from:

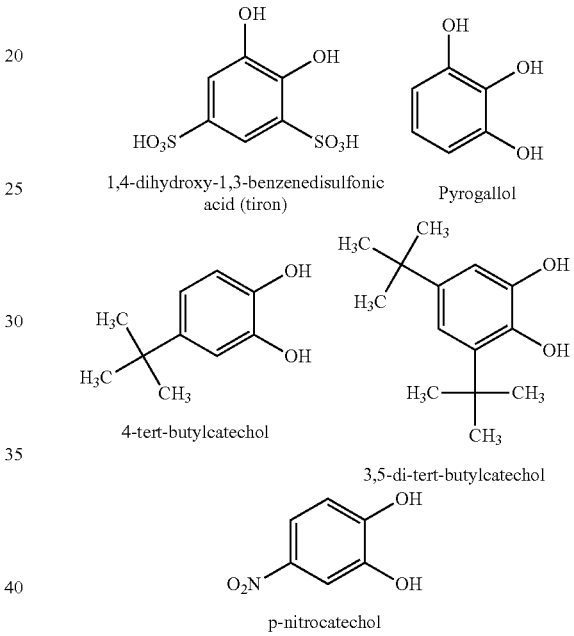

and/or their salt(s), and/or their mixtures, more preferably one or more compound according to group b2) is tiron and/or its salt(s).

It is preferred from the viewpoint of commercial availability that one or more compound(s) according to group b3) of composition B is according to the following general structure:

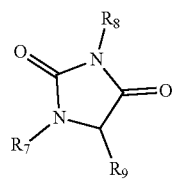

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

It is preferred from the viewpoint of commercial availability and dyeing intensity that one or more compound(s)

according to group b3) of composition B is hydantoin or allantoin, and/or their salt(s), and/or their mixtures, preferably it is hydantoin and/or its salt(s).

Thus, the disclosure of the present invention also is directed to a cosmetic product for dyeing of keratin fibers, preferably for dyeing of human keratin fibers, more preferably for dyeing of human hair, comprising:
- a composition A comprising one or more alkalizing agent(s) and one or more direct dye(s),
- an aqueous composition B having a pH in the range of 1 to 6 and comprising:
a) hydrogen peroxide, and
b) one or more compound(s) selected from the following groups:
1) caffeine and/or theobromine, and/or their mixtures,
2) tiron and/or its salt(s),
3) hydantoin and/or its salts,
and/or their mixtures.

It is further preferred from the viewpoint of stabilizing performance that the total concentration of compounds according to b) is 0.001% by weight or more, more preferably 0.005% by weight or more, further more preferably 0.01% by weight or more, still more preferably 0.03% by weight or more, calculated to the total weight of composition B.

It is further preferred from the viewpoint of economic reasons as well as stabilizing performance that the total concentration of compounds according to b) is 0.5% by weight or less, more preferably 0.25% by weight or less, further more preferably 0.2% by weight or less, still more preferably 0.15% by weight or less, calculated to the total weight of composition B.

For attaining the above-mentioned effects, it is preferred that It is preferred from the viewpoint of stabilization and dyeing intensity that that the total concentration of compounds according to b) is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of composition B.

It is preferred from the viewpoint of stabilization performance that the weight ratio of compounds a) to b) in composition B is 2 or more, more preferably 20 or more, further more preferably 37.5 or more, further more preferably 100 or more.

It is preferred from the viewpoint of stabilization performance that the weight ratio of compounds a) to b) in composition B is 1,000 or less, more preferably 600 or less, further more preferably 400 or less, further more preferably 150 or less.

For achieving the above-mentioned effects, it is preferred that the weight ratio of compounds a) to b) in composition B is in the range of 2 to 1,000, more preferably in the range of 20 to 600, further more preferably in the range of 37.5 to 400, further more preferably in the range of 100 to 150.

Forms of Composition B

Composition B of the present invention preferably is an emulsion, thickened gel, or a combination thereof, from the viewpoint of cosmetic safety as well as user friendliness. It may comprise lipophilic compound(s) according to group c) and/or surfactant(s) according to group d).

Lipophilic Compounds as Compounds According to Group c)

Compositions A and/or B of the present invention may be formulated as an emulsion and/or thickened emulsion. In this case, it is preferred that compositions A and/or B comprise(s) one or more lipophilic compound(s) as compound(s) according to group c).

Preferably, compounds according to group c) are selected from $C_{12}$ to $C_{22}$ fatty alcohols, esters of $C_3$ to $C_{22}$ alcohols with $C_{12}$ to $C_{22}$ fatty acids, Ca to $C_{22}$ fatty acids, vegetable oils, and/or silicones, and/or hydrocarbon-based products, and/or their mixtures, from the viewpoint of cosmetic compatibility.

Suitable $C_{12}$ to $C_{22}$ fatty alcohols are myristyl alcohol, cetyl alcohol, stearyl alcohol, behenyl alcohol, and cetearyl alcohol.

Suitable esters of $C_3$ to $C_{22}$ alcohols with $C_{12}$ to $C_{22}$ fatty acids are isopropyl myristate, isopropyl palmitate, and myristyl myristate.

Suitable $C_8$ to $C_{22}$ fatty acids are oleic acid, linoleic acid, and palmitic acid.

Suitable vegetable oils are olive oil, almond oil, sunflower oil, and argan oil.

Suitable silicones are non-aminated and/or aminated silicones. The latter are commonly known as amodimethicones.

It is preferred from the viewpoint of forming a stable composition and user friendliness that the total concentration of compounds according to group c) is 1% by weight or more, more preferably 2% by weight or more, further more preferably 3% by weight or more, calculated to the total weight of each of the compositions A and/or B.

It is preferred from the viewpoint of forming a stable composition that the total concentration of compounds according to group c) is 20% by weight or less, more preferably 15% by weight or less, further more preferably 12% by weight or less, calculated to the total weight of each of the compositions A and/or B.

For attaining the above-mentioned effects, the total concentration of compounds according to group c) is in the range of 1% to 20% by weight, preferably in the range of 2% to 15% by weight, more preferably in the range of 3% to 12% by weight, calculated to the total weight of each of the compositions A and/or B.

Surfactants as Compounds According to Group d)

The compositions A and/or B of the present invention may further comprise one or more surfactant(s) as compound according to group d), preferably selected from non-ionic surfactants, anionic surfactants, cationic surfactants, and/or amphoteric/zwitterionic surfactants, and/or their salt(s), and/or their mixtures, more preferably selected from anionic surfactants and/or their salt(s), from the viewpoint of stabilizing the composition and improving wettability and mixability.

Preferably, the anionic surfactants may be selected from ethoxylated or non-ethoxylated alkyl ether sulfate surfactants, alkyl sulfates, ethoxylated and/or non-ethoxylated alkyl carboxylates, ethoxylated or non-ethoxylated amino acid surfactants, and/or their mixtures, and/or their salts.

Suitable examples are alkyl sulfate or preferably ethoxylated alkyl ether sulfate surfactants or mixtures thereof, and/or salts thereof, having an alkyl chain length of $C_{10}$ to $C_{22}$ and an ethoxylation degree from 1 to 50.

Suitable non-ionic surfactants may be selected from alkyl polyglycosides, ethoxylated triglycerides, ethoxylated fatty alcohols, ethoxylated fatty acid esters, and/or their mixtures.

Suitable cationic surfactants are quaternary ammonium surfactants having a carbon chain length in the range of $C_{12}$ to $C_{22}$ or surfactants having a tertiary amine group and at least one alkyl chain having a carbon chain length in the range of $C_{12}$ to $C_{22}$ such as alkylamidoalkylamine surfactants, and/or their salts. Suitable examples are cetrimonium chloride and behentrimonium chloride.

Suitable amphoteric/zwitterionic surfactants are of betaine type. Suitable compounds may be selected from alkyl betaines and/or alkylamido betaines. A preferred compound selected from alkyl betaines is lauryl betaine. A preferred compound selected from alkylamido betaines is cocamidopropyl betaine. The disclosure also relates to the salts of the compounds.

Suitable concentration ranges for surfactants are in the range of 0.1% to 10% by weight, calculated to the total weight of each of the compositions A and/or B, from the viewpoint of enhancing wettability of keratin fibers, physical stability, and mixability with other compositions.

Thickening Polymers

From the viewpoint of cosmetic safety, it is further preferred that the compositions A and/or B of the present invention comprise(s) one or more thickening polymer(s).

The compositions A and/or B of the present invention may comprise(s) one or more thickening polymer(s) selected from non-ionic thickening polymers and/or anionic thickening polymers, and/or their mixtures.

Preferably, the thickening polymers are selected from polymers resulting in an aqueous solution and/or aqueous dispersion at pH between 1 and 6 having a viscosity of at least 1,000 mPa·s measured at a polymer concentration of 1% by weight in water at 25° C., calculated to the total weight of the composition, determined by a Brookfield viscometer, such as at 10 rpm for 1 min, with an appropriate spindle at 25° C.

Suitable non-ionic thickening polymers are cellulose-based polymers. Suitable examples of cellulose-based polymers are methylcellulose, hydroxymethylcellulose, hydroxyethylcellulose, hydroxypropylcellulose, hydroxyethyl-methylcellulose, and alkylated hydroxyl celluloses such as ($C_2$-$C_8$)-alkylcelluloses or cetyl hydroxyethylcellulose.

Suitable anionic thickening polymers are selected from naturally-based anionic polymers and/or synthetic anionic polymers.

Suitably, the natural anionic polymer(s) may be selected from xanthan gum, dehydroxanthan gum, hydroxypropylxanthan gum, carboxymethyl cellulose and starch based polymers such as vegetable starch and/or their synthetically modified derivatives such as hydroxypropyl starch phosphate. Equally suitable are alginic acids, sodium alginates, ammonium alginates, calcium alginates, gum arabic, and guar gum.

Suitable synthetic anionic polymers are associative thickening polymers, such as acrylates/steareth-30 methacrylate copolymer.

The preferred thickening polymer for the composition of the present invention are natural anionic polymers, more preferably xanthan gum and/or dehydroxanthan gum, from the viewpoint of their biodegradability and low environmental impact.

Preferably, the total concentration of thickening polymers in the compositions A and/or B of the present invention is/are 0.1% by weight or more, more preferably 0.25% by weight or more, more preferably 0.5% by weight or more, calculated to the total weight of each of the compositions A and/or B, from the viewpoint of providing sufficient viscosity to compositions A and/or B.

Preferably, the total concentration of thickening polymers in the compositions A and/or B of the present invention is 15% by weight or less, more preferably 12% by weight or more, further more preferably 10% by weight or less, calculated to the total weight of each of the compositions A and/or B, from the viewpoint of providing sufficient viscosity to the compositions A and/or B and cost of goods.

For attaining the above-mentioned effects, it is preferred that the total concentration of thickening polymers in the compositions A and/or B of the present invention is in the range of 0.1% to 15% by weight, preferably in the range of 0.25% to 12% by weight, more preferably in the range of 0.5% to 10% by weight, calculated to the total weight of each of the compositions A and/or B.

It is preferred from the viewpoint of cosmetic safety that the compositions A and/or B of the present invention has/have a viscosity in the range of 1,000 Pas to 25,000 mPas, preferably 2,000 mPas to 20,000 mPas, more preferably in the range of 2,500 mPas to 17,500 mPas, determined by cone plate viscometry at 25° C. under atmospheric conditions. A suitable viscometer is a Brookfield viscometer with spindle #4.

Kit-of-Parts

The present invention is also directed to a kit-of-parts comprising the compositions A and B as defined above and one more composition selected from:

a bleaching powder composition C comprising one or more persalt(s) and/or peroxy salt(s) and one or more alkalizing agent(s), an aqueous lightening composition D comprising one or more alkalizing agent(s) and having a pH in the range of 7 to 12, an aqueous dyeing composition E having a pH in the range of 7 to 12 and comprising one or more dye selected from oxidative dye precursor(s), oxidative dye coupler(s), and/or direct dye(s), and/or their salt(s), and/or their mixtures.

Bleaching Powder Composition C

It is further preferred that the bleaching powder composition C comprises one or more persalt(s) and/or peroxy salt(s) as bleaching compound(s) and one or more alkalizing agent(s).

Suitable persalts and/or peroxy salts are sodium persulfate, potassium persulfate, ammonium persulfate, earth alkali peroxides such as magnesium peroxide, melamine peroxide or urea peroxide or phthalimidoperoxy hexanoic acid. The preferred persalts from the viewpoint of bleaching power are sodium, potassium and ammonium persulfate.

It is preferred from the viewpoint of bleaching power and cosmetic safety that the total concentration of persalts and/or peroxy salts in the bleaching powder composition C is in the range of 10% to 80% by weight, preferably in the range of 15% to 70% by weight, more preferably in the range of 20% to 60% by weight, and still more preferably in the range of 25% to 60% by weight, calculated to the total weight of the bleaching powder composition C.

The bleaching powder composition C further comprises one or more alkalizing agent(s). Suitable alkalizing agent(s) are metasilicates and disilicates, in particular sodium metasilicate and/or sodium disilicate. It is preferred from the viewpoint of alkalinity that the concentration of metasilicates and/or disilicates, and/or their salts, in the bleaching powder composition C is in the range of 1% to 20% by weight, more preferably 5% to 15% by weight, calculated to the total weight of the bleaching powder composition C.

Other suitable alkalizing agent(s) are carbonate and bicarbonate alkali salts such as sodium, potassium, and ammonium salts. The preferred salts are bicarbonate salts and especially preferred is ammonium bicarbonate, from the viewpoint of buffer capacity. Suitable concentration of carbonates in the bleach powder composition is in the range of 0.25% to 10% by weight, preferably in the range of 0.5% to 7.5% by weight, more preferably in the range of 0.75% to 5% by weight, and still more preferably in the range of 1% to 4% by weight, calculated to the total weight of the bleaching powder composition C, from the viewpoint of buffer capacity and low hair damage.

Aqueous Lightening Composition D

Preferably, the aqueous lightening composition D is an emulsion comprising one or more lipophilic compound(s) according to group c), as also disclosed for the compositions A and/or B, from the viewpoint of user convenience.

The aqueous lightening composition preferably has a pH in the range of 8 to 11, more preferably in the range of 8.5 to 10.5, from the viewpoint of lightening performance. Suitable alkalizing agents are disclosed below for the aqueous dyeing composition E.

Aqueous Dyeing Composition E

The aqueous dyeing composition E comprises one or more oxidative dye precursors, for example, p-phenylendiamine and/or its derivatives, p-aminophenol and/or its derivatives, and heterocyclic compounds such as diaminopyrazols and substituted pyrimidines and/or their derivatives and/or their salts.

Furthermore, besides oxidative dye precursors, aqueous dyeing composition E comprises oxidative dye couplers. Suitable oxidative dye couplers are resorcinol and/or its derivatives, m-aminophenol and/or its derivatives, m-phenylenediamine and/or its derivatives, pyridines and/or its derivatives, and naphthol and/or its derivatives, and/or their salts.

Furthermore, the aqueous dyeing composition E may comprise one or more hair direct dye(s).

The suitable total concentration of oxidative dye precursors and/or oxidative dye couplers and/or direct dyes is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of the aqueous dyeing composition D.

Suitably, the aqueous dyeing composition E comprises one or more alkalizing agent. Preferably, one or more alkalizing agent(s) is selected from ammonia, alkyl- or alkanolamines according to the general structure

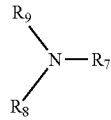

wherein $R_7$, $R_8$, and $R_9$ are same or different H, from $C_1$ to $C_4$ alkyl, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_7$, $R_8$, or $R_9$ is different from H.

It is preferred from the viewpoint of dyeing intensity that the alkalizing agent is selected from ammonia and/or monoethanolamine and/or 2-aminomethyl propanol and/or tris-(hydroxymethyl)-aminomethane.

It is further preferred from the viewpoint of sufficient alkalinity and dyeing intensity that the total concentration of alkalizing agents in the aqueous dyeing composition E is in the range of 0.25% to 15% by weight, more preferably in the range of 0.5% to 12.5% by weight, still more preferably in the range of 0.75% to 10% by weight, and still more preferably in the range of 1% to 7.5% by weight, calculated to the total weight of the aqueous dyeing composition E.

The aqueous dyeing composition E has a pH in the range of 7 to 12. It is preferred from the viewpoint of buffering capacity that the pH of the aqueous dyeing composition E is in the range of 7.5 to 11, more preferably in the range of 8.0 to 10, still more preferably in the range of 8.5 to 9.5.

Method for Dyeing

The present invention is also directed to a method for dyeing of keratin fibers, preferably human keratin fibers, more preferably human hair, comprising the steps of:
i) providing compositions A and B as defined above,
ii) mixing the compositions to yield a ready-to-use composition having a pH in the range of 7 to 12,
iii) applying the ready-to-use composition onto keratin fibers
iv) leaving it for a time period of 1 to 60 min and optionally heating the keratin fibers to a temperature range in the range of 40° C. to 60° C.
v) rinsing off the keratin fibers and optionally shampooing the keratin fibers.

Suitably, the pH of the ready-to-use composition is in the range of 7 to 12. It is preferred from the viewpoint of accelerated dyeing that the pH of the ready-to-use composition is in the range of 7.5 to 11, more preferably 8.0 to 10.5.

The ready-to-use composition is then applied to keratin fibers and left for a time period of 1 min to 60 min as defined in step iv). Preferred time ranges for step iv) are 5 min to 45 min, more preferred ranges are 10 min to 35 min, from the viewpoint of sufficiently bleaching/lightening.

Optionally, heat may be applied while leaving the ready-to-use composition onto keratin fibers. Suitable temperature ranges are 30° C. to 50° C.

Use of Compounds

The present invention is also directed to a use of one or more compound(s) selected from:

1)

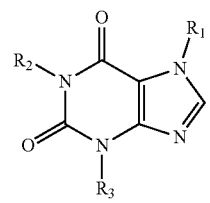

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s),
for improving color intensity and/or wash fastness of direct dyes on keratin fibers, preferably on human keratin fibers, more preferably on human hair.
for improving color intensity and/or wash fastness of direct dyes on keratin fibers, preferably on human keratin fibers, more preferably on human hair.

It is preferred from the viewpoint of stabilization that one or more compound (s) according to 1) is one or more compound(s) as defined as b1) above.

It is preferred from the viewpoint of stabilization that one or more compound (s) according to 2) is one or more compound(s) as defined as b2) above.

It is preferred from the viewpoint of stabilization that one or more compound (s) according to 3) is one or more compound(s) as defined as b3) above.

The present disclosure is also directed to <1> a cosmetic product for dyeing of keratin fibers, preferably for dyeing of human keratin fibers, more preferably for dyeing of human hair, comprising:
a composition A comprising one or more alkalizing agent(s) and one or more direct dye(s),
an aqueous composition B having a pH in the range of 1 to 6 and comprising:
a) hydrogen peroxide, and
b) one or more compound(s) selected from the following groups:
a) hydrogen peroxide, and
b) one or more compound(s) selected from the following groups:

1)

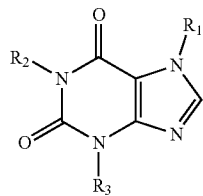

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s).

<2> The product according to clause <1> characterized in that the one or more alkalizing agent(s) of composition A is/are one or more organic alkalizing agent(s) and/or its/their salt(s), and/or ammonia, and/or its salt(s).

<3> The product according to any of the clauses <1> to <2> characterized in that one or more organic alkalizing agent(s) of composition A is/are selected from alkyl and/or alkanolamine(s) and/or its/their salt(s), more preferably they/it is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane and/or its/their salt(s), and/or their mixtures.

<4> The product according to any of the clauses <1> to <3> characterized in that the one or more alkalizing agent(s) of composition A is selected from monoethanolamine, 2-amino-2-methylpropanol, tris-(hydroxymethyl)-aminomethane, and/or its/their salt(s), ammonia and or its salt(s), and/or their mixtures.

<5> The product according to any of the clauses <1> to <4> characterized in that the one or more alkalizing agent(s) of composition A is one or more inorganic alkalizing agent(s), preferably selected from metasilicates, carbonates, and/or bicarbonates, and/or their alkali or earth alkali salts, and/or their mixtures, more preferably it is sodium metasilicate.

<6> The product according to any of the clauses <1> to <5> characterized in that the total concentration of alkalizing agent(s), preferably the total concentration of one or more alkanolamine(s) and/or its/their salt(s) and/or ammonia and/or its salt(s), is in the range of 0.1% to 40% by weight, preferably in the range of 0.25% to 30% by weight, more preferably in the range of 0.5% to 25% by weight, calculated to the total weight of composition A.

<7> The product according to any of the clauses <1> to <6> characterized in that the one or more direct dye(s) of composition A are selected from anionic, cationic, or neutral direct dyes, and/or their salt(s), and/or their mixtures.

<8> The product according to any of the clauses <1> to <7> characterized in that one or more anionic direct dyes is/are Acid Black 1, Acid Blue 1, Acid Blue 3, Food Blue 5, Acid Blue 7, Acid Blue 9, Acid Blue 74, Acid Orange 3, Acid Orange 6, Acid Orange 7, Acid Orange 10, Acid Red 1, Acid Red 14, Acid Red 18, Acid Red 27, Acid Red 50, Acid Red 52, Acid Red 73, Acid Red 87, Acid Red 88, Acid Red 92, Acid Red 155, Acid Red 180, Acid Violet 9, Acid Violet 43, Acid Violet 49, Acid Yellow 1, Acid Yellow 23, Acid Yellow 3, Food Yellow No. 8, D&C Brown No. 1, D&C Green No. 5, D&C Green No. 8, D&C Orange No. 4, D&C Orange No. 10, D&C Orange No. 11, D&C Red No. 21, D&C Red No. 27, D&C Red No. 33, D&C Violet 2, D&C Yellow No. 7, D&C Yellow No. 8, D&C Yellow No. 10, FD&C Red 2, FD&C Red 40, FD&C Red No. 4, FD&C Yellow No. 6, FD&C Blue 1, Food Black 1, Food Black 2, Disperse Black 9 and Disperse Violet 1 and their alkali metal salts such as sodium, potassium. Among those, the most preferred anionic dyestuffs are Acid Red 52, DC Violet 2, DC Red 33, DC Orange 4, DC Red 27, DC Yellow 10, HC Blue 18, HC Red 18, and HC Yellow 16, and/or their salt(s), and/or their mixtures.

<9> The product according to any of the clauses <1> to <8> characterized in that one or more cationic dye(s) is/are Basic Blue 6, Basic Blue 7, Basic Blue 9, Basic Blue 26, Basic Blue 41, Basic Blue 99, Basic Brown 4, Basic Brown 16, Basic Brown 17, Natural Brown 7, Basic Green 1, Basic Red 2, Basic Red 12 Basic Red 22, Basic Red 76, Basic Violet 1, Basic Violet 2, Basic Violet 3, Basic Violet 10, Basic Violet 14, Basic Yellow 57, Basic Red 51, Basic Yellow 87, HC Blue 17 and Basic Orange 31. The most preferred ones are Basic Red 51, Basic Yellow 87 Basic Orange 31, HC Blue 17 and Basic Blue 124, and/or their salt(s), and/or their mixtures.

<10> The product according to any of the clauses <1> to <9> characterized in that one or more neutral dye(s) is/are HC Blue No. 2, HC Blue No. 4, HC Blue No. 5, HC Blue No. 6, HC Blue No. 7, HC Blue No. 8, HC Blue No. 9, HC Blue No. 10, HC Blue No. 11, HC Blue No. 12, HC Blue No. 13, HC Brown No. 1, HC Brown No. 2, HC Green No. 1, HC Orange No. 1, HC Orange No. 2, HC Orange No. 3, HC Orange No. 5, HC Red BN, HC Red No. 1, HC Red No. 3, HC Red No. 7, HC Red No. 8, HC Red No. 9, HC Red No. 10, HC Red No. 11, HC Red No. 13, HC Red No. 54, HC Red No. 14, HC Violet BS, HC Violet No. 1, HC Violet No. 2, HC Yellow No. 2, HC Yellow No. 4, HC Yellow No. 5, HC Yellow No. 6, HC Yellow No. 7, HC Yellow No. 8, HC Yellow No. 9, HC Yellow No. 10, HC Yellow No. 11, HC Yellow No. 12, HC Yellow No. 13, HC Yellow No. 14, HC Yellow No. 15, 2-amino-6-chloro-4-nitrophenol, picramic acid, 1, and 2-hydroxyethylpicramic acid, and/or their mixtures.

<11> The product according to any of the clauses <1> to <10> characterized in that one or more direct dye(s) is selected from HC Blue 18, HC Red 18, HC Yellow 16, Disperse Black 9, Acid Yellow 1, 2-amino-6-chloro-4-nitrophenol, and/or their salt(s), and/or their mixtures.

<12> The product according to any of the clauses <1> to <11> characterized in that the total concentration of direct dyes in composition A is in the range of 0.001% to 10% by weight, preferably in the range of 0.005% to 5% by weight, more preferably in the range of 0.01% to 3% by weight, still further more preferably in the range of 0.01% to 1.5% by weight, still further more preferably in the range of 0.01% to 1% by weight, calculated to the total weight of composition A.

<13> The product according to any of the clauses <1> to <12> characterized in that the composition A is an aqueous composition.

<14> The product according to clause <13> characterized in that the total concentration of water in composition A is in the range of 50% to 98% by weight, more preferably in the range of 60% to 95% by weight, further more preferably in the range of 70% to 92% by weight, still more preferably in the range of 80% to 92% by weight, calculated to the total weight of composition A.

<15> The product according to any of the clauses <13> to <14> characterized in that the pH of composition A is in the range of 7 to 12, preferably in the range of 7.5 to 11, more preferably in the range of 8 to 10.5, further more preferably in the range of 9 to 10.5.

<16> The product according to any of the clauses <1> to <12> characterized in that composition A is a liquid composition at 25° C. and atmospheric pressure comprising one or more organic solvent(s) as compound(s) and less than 1% by weight of water, calculated to the total weight of composition A.

<17> The product according to clause <16> characterized in that composition A is anhydrous.

<18> The product according to any of the clauses <16> to <17> characterized in that organic solvent(s) of composition A are mono-, di-, and trivalent alcohols and/or their mixtures.

<19> The product according to any of the clauses <16> to <18> characterized in that the organic solvent(s) of composition A is/are ethanol, n-propanol, isopropanol, propylene glycol, ethylene glycol, benzyl alcohol, phenoxyethanol, and glycerol, and/or their mixtures.

<20> The product according to any of the clauses <16> to <19> characterized in that the total concentration of organic solvents in composition A is in the range of 75% to 98% by weight, more preferably 80% to 95% by weight, further more preferably in the range of 85% to 92% by weight, calculated to the total weight of composition A.

<21> The product according to any of the clauses <1> to <12> characterized in that composition A is a powder composition.

<22> The product according to clause <21> characterized in that composition A comprises water at 10% by weight or less, calculated to the total weight of composition A, preferably it is anhydrous.

<23> The product according to any of the clauses <21> to <22> characterized in that composition A comprises one or more pulverulent excipient.

<24> The product according to clause <23> characterized in that composition A comprises one or more organic and/or an inorganic pulverulent excipient.

<25> The product according to clause <24> characterized in that the organic and/or an inorganic pulverulent excipients is/are diatomaceous earth, kaolin, bentonite, starch especially corn, tapioca, rice, wheat and potato, nylon powder, montmorillonit, gypsum, sawdust and perlite.

<26> The product according to any of the clauses <23> to <25> characterized in that the total concentration of organic and/or an inorganic pulverulent excipient in composition A is in the range of 50% to 98% by weight, more preferably in the range of 55% to 95% by weight, further more preferably in the range of 60% to 90% by weight, still further more preferably 65% to 90% by weight, still further more preferably 70% to 90% by weight, even more preferably 75% to 90% by weight, calculated to the total weight of composition A.

<27> The product according to any of the clauses <1> to <26> characterized in that the pH of the composition B is in the range of 1.25 to 5, more preferably in the range of 1.5 to 4, further more preferably in the range of 2 to 3.

<28> The product according to any of the clauses <1> to <27> characterized in that the concentration of the compound according to group a) in the composition B is in the range of more than 0.1% to 20% by weight, more preferably in the range of 0.25% to 15% by weight, further more preferably in the range of 1% to 12% by weight, calculated to the total weight of composition B.

<29> The product according to any of the clauses <1> to <28> characterized in that one or more compound(s) according to group b1) of composition B is/are xanthine and/or xanthine derivatives, preferably xanthine, theobromine, theophylline, caffeine, and/or their mixtures.

<30> The product according to any of the clauses <1> to <29> characterized in that one or more compound(s) according to group b1) of composition B is/are is/are caffeine and/or theobromine, and/or their mixtures, preferably it is caffeine.

<31> The product according to any of the clauses <1> to <28> characterized in that one or more compound(s) according to group b2) of composition B is selected from Flavonols,
Anthocyanidines,
Anthocyanines or anthocyanes,
Orthohydroxybenzoates,
Flavones,
Hydroxystilbenes,
3,4-dihydroxyphenylalanine and its derivatives,
2,3-dihydroxyphenylalanine and its derivatives,
4,5-dihydroxyphenylalanine and its derivatives,
Dihydroxycinnamates,
Orthopolyhydroxycoumarines,
Orhtopolyhydroxyisocoumarines,
Orthopolyhydroxycoumarones,
Orthopolyhydroxyisocoumarones,
Orhtopolyhydroxychalcones,
Orhtopolyhydroxychromones,
Orhtopolyhydroxyquinones,
Orhtohydroxyxanthones,
1,2-dihyroxybenzenes and its derivatives,
1,2,4-trihydroxybenzenes and its derivatives,
1,2,3-trihydroxybenzenes and its derivatives,
2,4,5-trihydroxybenzenes and its derivatives,
Proanthocyanidines,
Proanthocyanines,
Tannic acid,
Ellagic acid,
one or more compound(s) according the following general structure:

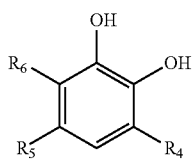

wherein $R_4$, $R_5$, and $R_6$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl, and/or their salt(s), and/or their mixture(s).

<32> The product according to any of the clauses <1> to <28> and <31> characterized in that for group b2) of composition B one or more compound(s) is according to the following general structure:

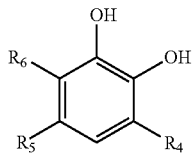

wherein $R_4$, $R_5$, and $R_6$ are independently selected from H, OH, halogen, $C_1$-$C_{12}$ linear or branched alkyl or alkenyl, O—X, $NO_2$, COOH, $SO_3H$, aryl, heteroaryl, and/or their salt(s), and/or their mixtures, with X being $C_1$-$C_{12}$ linear or branched alkyl.

<33> The product according to any of the clauses <1> to <28> and/or <31> to <32> characterized in that for group b2) of composition B $R_4$ is selected from H, OH, halogen, $C_1$-$C_{12}$ linear or branched alkyl or alkenyl, O—X, $NO_2$, COOH, $SO_3H$, aryl, heteroaryl, with X being $C_1$-$C_{12}$ linear or branched alkyl, and $R_5$, and $R_6$ are independently selected from $C_1$-$C_{12}$ linear or branched alkyl or alkenyl, O—X, $NO_2$, COOH, $SO_3H$, and/or their salt(s), and/or their mixtures, with X being $C_1$-$C_{12}$ linear or branched alkyl.

<34> The product according to any of the clauses <1> to <28> and <31> to <33> characterized in that at least one compound according to group b2) of composition B is selected from:

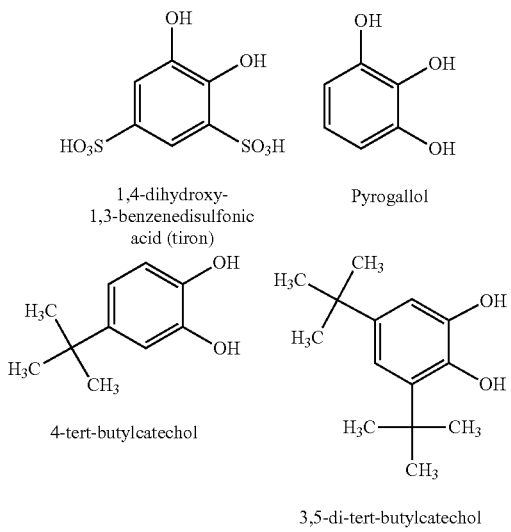

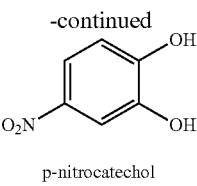

p-nitrocatechol and/or their salt(s), and/or their mixtures.

<35> The product according to any of the clauses <1> to <28> and <31> to <34> characterized in that one more compound according to group b2) of composition B is tiron and/or its salt(s).

<36> The product according to any of the clauses <1> to <28> and <31> to <35> characterized in that the total concentration of compounds according to group b1) of composition B is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition B.

<37> The product according to any of the clauses <1> to <28> and <31> to <36> characterized in that the total concentration of tiron and/or its salt(s) in composition B is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of the composition B.

<38> The product according to any of the clauses <1> to <28> characterized in that one or more compound(s) according to group b3) of composition B is according to the following general structure:

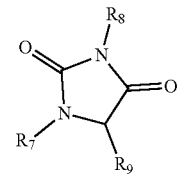

wherein $R_7$, $R_8$, and $R_9$ are independently selected from H, OH, halogen, $C_1$-$C_{12}$ linear or branched alkyl or alkenyl, O—X, COOH, phenyl, diphenyl, ureyl, and/or their salt(s), and/or their mixtures, with X being $C_1$-$C_{12}$ linear or branched alkyl.

<39> The product according to any of the clauses <1> to <28> and <38> characterized in that one or more compound(s) according to group b3) of composition B is:
hydantoin,
dichlordimethylhydantoin,
bromchlordimethylhydantoin,
dibromdimethylhydantoin,
ethotoin,
phenytoin,
mephenytoin,
fosphenytoin,
allantoin,
and/or their salt(s), and/or their mixtures.

<40> The product according to any of the clauses <1> to <28> and <38> to <39> characterized in that one or more compound(s) according to group b3) of composition B is hydantoin or allantoin, and/or their salt(s), and/or their mixtures.

<41> The product according to any of the clauses <1> to <28> and <38> to <40> characterized in that one or more compound(s) according to group b3) of composition B is hydantoin and/or its salt(s).

<42> The product according to any of the clauses <1> to <28> and <38> to <41> characterized in that the total concentration of compounds according to b3) of composition B is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of composition B.

<43> The product according to any of the clauses <1> to <28> and <38> to <42> characterized in that the total concentration of hydantoin and/or its salt(s) in composition B is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of composition B.

<44> The product according to any of the clauses <1> to 43> characterized in that the total concentration of compounds according to group b) in composition B is in the range of 0.001% to 0.5% by weight, preferably in the range of 0.005% to 0.25% by weight, more preferably in the range of 0.01% to 0.2% by weight, still more preferably in the range of 0.03% to 0.15% by weight, calculated to the total weight of composition B.

<45> The product according to any of the clauses <1> to <44> characterized in that the weight ratio of compounds according to groups a) to b) in composition B is in the range of 2 to 1,000, more preferably in the range of 20 to 600, further more preferably in the range of 37.5 to 400, further more preferably in the range of 100 to 150.

<46> The product according to any of the clauses <1> to <45> characterized in that the weight ratio of compounds according to groups a) to b1) in composition B is in the range of 2 to 1,000, more preferably in the range of 20 to 600, further more preferably in the range of 37.5 to 400, further more preferably in the range of 100 to 150.

<47> The product according to any of the clauses <1> to <28> and/or <31> to <37> characterized in that the weight ratio of compounds according to group a) to b2) in composition B is in the range of 2 to 1,000, more preferably in the range of 20 to 600, further more preferably in the range of 37.5 to 400, further more preferably in the range of 100 to 150.

<48> The product according to any of the clauses <1> to <28> and/or <38> to <43> characterized in that the weight ratio of compounds according to groups a) to b3) in composition B is in the range of 2 to 1,000, more preferably in the range of 20 to 600, further more preferably in the range of 37.5 to 400, further more preferably in the range of 100 to 150.

<49> The product according to any of the clauses <1> to <48> characterized in that composition B is a thickened gel and/or an emulsion.

<50> The product according to any of the clauses <1> to <49> characterized in that composition B comprises one or more lipophilic compound(s) as compound(s) according to group c).

<51> The product according to clause <50> characterized in that one or more compound(s) according to group c) is selected from $C_{12}$ to $C_{22}$ fatty alcohols, esters of $C_3$ to $C_{22}$ alcohols with $C_{12}$ to $C_{22}$ fatty acids, $C_8$ to $C_{22}$ fatty acids, vegetable oils, and/or silicones, and/or hydrocarbon-based products, and/or their mixtures.

<52> The product according to any of the clauses <50> and/or <51> characterized in that the total concentration of compounds according to group c) in composition B is in the range of 1% to 20% by weight, preferably in the range of 2% to 15% by weight, more preferably in the range of 3% to 12% by weight, calculated to the total weight of composition B.

<53> The product according to any of the clauses <1> to <52> characterized in that composition B comprises one or more surfactant(s) as compound(s) according to group d), preferably selected from non-ionic surfactants, anionic surfactants, cationic surfactants, and/or amphoteric/zwitterionic surfactants, and/or their salt(s), and/or their mixtures, more preferably selected from anionic surfactants and/or their salt(s).

<54> The product according to clause <53> characterized in that the total concentration of one or more compound(s) according to group d) in composition B is in the range of 0.1% to 10% by weight, calculated to the total weight of composition B.

<55> The product according to any of the clauses <1> to <54> characterized in that the compositions A and/or B comprise(s) one or more thickening polymer.

<56> The product according to clause <55> characterized in that one or more thickening polymer(s) is/are selected from non-ionic thickening polymers and/or anionic thickening polymers, and/or their mixtures, and/or their salt(s).

<57> The product according to any of the clauses <55> to <56> characterized in that the total concentration of thickening polymers the compositions A and/or B is in the range of 0.1% to 15% by weight, preferably in the range of 0.25% to 12% by weight, more preferably in the range of 0.5% to 10% by weight, calculated to the total weight of each of the compositions A and/or B.

The present disclosure is also directed to <58> a kit-of-parts comprising the compositions A and B as defined in any of the clauses <1> to <57> and one more composition selected from:
  a bleaching powder composition C comprising one or more persalt(s) and/or peroxy salt(s) and one or more alkalizing agent(s),
  an aqueous lightening composition D comprising one or more alkalizing agent(s) and having a pH in the range of 7 to 12,
  an aqueous dyeing composition E having a pH in the range of 7 to 12 and comprising one or more dye selected from oxidative dye precursor(s), oxidative dye coupler(s), and/or direct dye(s), and/or their salt(s), and/or their mixtures.

<59> The kit-of-parts according to clause <58> characterized in that the compositions are separately packed.

<60> The kit-of-parts according to any of the clauses <58> and/or <59> characterized in that the total concentration of persalts and/or peroxy salts in the bleaching powder composition C is in the range of 10% to 80% by weight, preferably in the range of 15% to 70% by weight, more preferably in the range of 20% to 60% by weight, and still more preferably in the range of 25% to 60% by weight, calculated to the total weight of the bleaching powder composition C.

<61> The kit-of-parts according to any of the clauses <58> to <60> characterized in that the bleaching powder composition C further comprises one or more alkalizing agent(s).

<62> The kit-of-parts according to clause <61> characterized in that the alkalizing agent(s) of the bleaching powder composition C is/are metasilicates and/or disilicates and/or its/their salt(s), preferably sodium metasilicate or sodium disilicate.

<63> The kit-of-parts according to clauses <62> characterized in that the concentration of metasilicates and/or disilicates and/or its/their salt(s) in the bleaching powder composition C is in the range of 1% to 20% by weight, more preferably 5% to 15% by weight, calculated to the total weight of the bleaching powder composition C.

<64> The kit-of-parts according to any of the clauses <58> to <59> characterized in that the aqueous lightening composition D is an emulsion comprising one or more lipophilic compound(s) according to group c).

<65> The kit-of-parts according to any of the clauses <58>, <59>, and <64> characterized in that the aqueous lightening composition D has a pH in the range of 8 to 11, more preferably in the range of 8.5 to 10.5.

<66> The kit-of-parts according to any of the clauses <58> and/or <59> characterized in that the aqueous dyeing composition E comprises oxidative dye precursors, preferably p-phenylendiamine and/or its derivatives, p-aminophenol and/or its derivatives, and heterocyclic compounds such as diaminopyrazols and substituted pyrimidines, and/or their derivatives, and/or their salts.

<67> The kit-of-parts according to any of the clauses <58> to <59>, and <66> characterized in that the aqueous dyeing composition E comprises oxidative dye couplers, preferably resorcinol and/or its derivatives, m-aminophenol and/or its derivatives, m-phenylenediamine and/or its derivatives, pyridines and/or its derivatives, and naphthol and/or its derivatives, and/or their salts.

<68> The kit-of-parts according to any of the clauses <58> to <59>, and <66> to <67> characterized in that the total concentration of oxidative dye precursors and/or oxidative dye couplers and/or direct dyes is in the range of 0.001% to 5% by weight, preferably in the range of 0.01% to 4% by weight, more preferably in the range of 0.05% to 3% by weight, still more preferably in the range of 0.1% to 2% by weight, calculated to the total weight of aqueous dyeing composition E.

<69> The kit-of-parts according to any of the clauses <58> to <59>, and <66> to <68> characterized in that the aqueous dyeing composition E comprises one or more alkalizing agent, preferably one or more alkalizing agent(s) selected from ammonia, alkyl- or alkanolamines according to the general structure

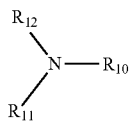

wherein $R_{10}$, $R_{11}$, and $R_{12}$ are same or different H, from $C_1$ to $C_4$ alkyl, $C_3$ to $C_4$ unsaturated alkyl, $C_3$ to $C_4$ branched alkyl, $C_1$ to $C_4$ hydroxyl alkyl, $C_3$ to $C_4$ unsaturated hydroxyl alkyl, $C_3$ to $C_4$ branched hydroxyl alkyl, with the condition that at least one of $R_{10}$, $R_{11}$, or $R_{12}$ is different from H.

<70> The kit-of-parts according to any of the clauses <58> to <59>, and <66> to <69> characterized in that one or more alkalizing agent of the aqueous dyeing composition E is selected from ammonia and/or monoethanolamine and/or 2-aminomethyl propanol, tris-(hydroxymethyl)-aminomethan and/or their salt(s), and/or their mixtures.

<71> The kit-of-parts according to any of the clauses <58> to <59> and <66> to <70> characterized in that the total concentration of alkalizing agent in the aqueous dyeing composition E is in the range of 0.25% to 15% by weight, more preferably in the range of 0.5% to 12.5% by weight, still more preferably in the range of 0.75% to 10% by weight, and still more preferably in the range of 1% to 7.5% by weight, calculated to the total weight of the aqueous dyeing composition E.

<72> The kit-of-parts according to any of the clauses <58> to <59> and <66> to <71> characterized in that the pH of the aqueous dyeing composition E is in the range of 7.5 to 11, more preferably in the range of 8.0 to 10, still more preferably in the range of 8.5 to 9.5.

The present disclosure is also directed to <73> a method for dyeing of keratin fibers, preferably human keratin fibers, more preferably human hair, comprising the steps of:
i) providing the compositions A and B as defined in any of the clauses <1> to <57>,
ii) mixing the compositions to yield a ready-to-use composition having a pH in the range of 7 to 12,
iii) applying the ready-to-use composition onto keratin fibers
iv) leaving it for a time period of 1 to 60 min and optionally heating the keratin fibers to a temperature range in the range of 40° C. to 60° C.
v) rinsing off the keratin fibers and optionally shampooing the keratin fibers.

<74> The method according to clause <73> characterized in that the ready-to-use composition of steps ii) and iii) has a pH in the range of 7 to 12, preferably in the range of 7.5 to 11, more preferably in the range of 8.0 to 10.5.

<75> The method according to any of the clauses <73> to <74> characterized in that ready-to-use composition in step iv) is left onto keratin fibers for a time period of 1 min to 60 min, preferably for a time period of 5 min to 45 min, more preferably for a time period of 10 min to 35 min.

<76> The method according to any of the clauses <73> to <75> characterized in that during the application time of the ready-to-use mixture in step iv), heat may be applied to the keratin fibers, preferably in a temperature range from 30° C. to 50° C.

The present disclosure is also directed to <77> a use of one or more compound(s) selected from:

1)

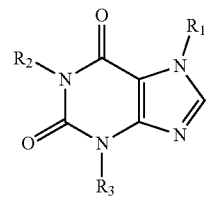

wherein $R_1$, $R_2$, and $R_3$ are independently selected from H and $CH_3$, and/or their mixtures,
2) one or more orthodiphenol(s) and/or their derivatives, and/or their mixtures, and/or their salt(s),
3) one or more imidazolidin-2,4-dione(s) and/or their derivatives, and/or their mixtures, and/or their salt(s), for improving color intensity and/or wash fastness of direct dyes on keratin fibers, preferably on human keratin fibers, more preferably on human hair.

<78> Use according to clause <77> characterized in that one or more compound (s) according to 1) is one or more compound(s) as defined as b1) in any of the clauses <1> and <29> to <30>.

<79> Use according to any of the clauses <77> to <78> characterized in that one or more compound (s) according to 2) is one or more compound(s) as defined as b2) in any of the clauses <1> and <31> to <37>.

<80> Use according to any of the clauses <77> to <79> characterized in that one or more compound (s) according to 3) is one or more compound(s) as defined as b3) in any of the clauses <1> and <38> to <43>.

The following examples are to illustrate the invention, but not to limit it.

EXAMPLES

Example 1

The following compositions B were prepared by dissolving the compounds according to group b) in an aqueous solution of hydrogen peroxide under constant stirring:

| | Ingredient | Inv. 1 | Inv. 2 | Inv. 3 | Inv. 4 | Comp. 1 |
|---|---|---|---|---|---|---|
| | | | | % by weight | | |
| Second comp. B | b1) Caffeine | 0.05 | — | — | — | — |
| | b1) Theoromine | — | 0.05 | — | — | — |
| | b2) Tiron | — | — | 0.05 | — | — |
| | b3) Hydantoin | — | — | — | 0.05 | — |
| | a) Hydrogen peroxide | 6.0 | | | | |
| | — Phosphoric acid | q.s. ad pH 2.5 | | | | |
| | — Water | Ad 100.0 | | | | |

The compositions were prepared and stored under controlled conditions at 40° C. for 20 days. Hydrogen peroxide content was analyzed by titration and the following concentrations were measured:

| Time [days] | Inv. 1 | Inv. 2 | Inv. 3 | Inv. 4 | Comp. 1 |
|---|---|---|---|---|---|
| | | | % by weight | | |
| 0 | 5.93 | 5.94 | 5.96 | 5.96 | 5.96 |
| 1 | 5.90 | 5.93 | 5.91 | 5.88 | 5.86 |
| 5 | 5.90 | 5.91 | 5.90 | 5.86 | 5.09 |
| 8 | 5.87 | 5.87 | 5.88 | 5.86 | 5.07 |
| 12 | 5.83 | 5.84 | 5.88 | 5.82 | 4.71 |
| 20 | 5.83 | 5.76 | 5.86 | 5.76 | 3.48 |

As a result, the compounds according to b) could maintain more than 96% of hydrogen peroxide activity over 20 days, whereas the comparative composition without compound according to b) was only 58% active after 20 days.

Inventive composition 1 and comparative composition 1, both after 20 days of storage, were then mixed with the following first composition A in a weight ratio 0.4:1 (Composition A:Composition B) to form a ready-to-use composition having a pH in the range of 10.0.

| Composition A | |
|---|---|
| Ingredient | % by weight |
| Aminomethyl propanol | 5.0 |
| HC Red 18 | 2.0 |
| HC Yellow 16 | 0.5 |
| Fragrance | q.s. |
| 1,2-propylene glycol | to 100 |

The following dyeing results were obtained:

| Treatment groups | Dyeing intensity, $\Delta E$ | Wash fastness, $\Delta\Delta E$ |
|---|---|---|
| Inv. 1 | 63.48 | 4.98 |
| Comp. 1 | 59.75 | 9.45 |

As illustrated by the results above, inventive composition 1 delivered a higher dyeing intensity and improved wash fastness in comparison to the comparative composition 1.

Methods

Hydrogen Peroxide Concentration

Hydrogen peroxide concentration was measured by iodometric titration using a Mettler Toledo DL58 titrator equipped with a Redox electrode and a 0.1N sodium-thiosulfate-solution.

Hair Dyeing

To human hairstreaks (21 cm, 2 g per bundle) were applied the ready-to-use compositions as explained above and left for 30 min at room temperature. The hairstreaks were then rinsed-off with lukewarm water, shampooed with a shampoo commercially available under the trade name Goldwell Deep Cleansing Shampoo, and blow-dried. The color was measured as outlined below.

Wash fastness was determined by placing the dyed hair streaks in a water bath comprising 5% by weight of sodium laureth sulfate and shaking it for 30 min at 40° C.

After this treatment, the hairstreak were blow-dried and the remaining color was measured ($\Delta\Delta E$).

The colormetric data were obtained with a color-difference meter by the CIE colorimetric system (L*,a*,b*), and the color difference ($\Delta E$) were calculated by the following formula.

$$\Delta E = \sqrt{(L_1^* - L_0^*)^2 + (a_1^* - a_0^*)^2 + (b_1^* - b_0^*)^2}$$

The following examples are within the scope of the present invention.

| Example 2 | |
|---|---|
| | % by weight |
| Composition A | |
| Hydroxyethylcellulose | 3 |
| Tetrasodium EDTA | 2 |
| Sodium carbonate | 1 |
| Ammonium persulfate | 11 |
| Potassium persulfate | 36 |
| Sodium metasilicate | 10 |
| HC Blue 18 | 0.2 |
| HC Red 18 | 0.05 |
| HC Yellow 16 | 0.01 |

-continued

Example 2

|  | % by weight |
|---|---|
| Mineral oil | 8 |
| Diatomaceous Earth | to 100 |
| Composition B |  |
| Cetearyl alcohol | 4.0 |
| Sodium lauryl sulfate | 0.8 |
| Phosphoric acid | q.s. ad pH 2.5 |
| Tiron disodium salt | 0.05 |
| Hydrogen peroxide | 9.0 |
| Water | ad 100.0 |

Example 3

|  | % by weight |
|---|---|
| Composition A |  |
| Aminomethyl propanol | 5.0 |
| HC Red 18 | 0.4 |
| HC Yellow 16 | 0.1 |
| HC Blue 18 | 1.0 |
| Fragrance | q.s. |
| Diatomaceous Earth | to 100 |
| Composition B |  |
| Cetearyl alcohol | 4.0 |
| Sodium lauryl sulfate | 0.8 |
| Phosphoric acid | q.s. ad pH 2.5 |
| Hydantoin | 0.05 |
| Hydrogen peroxide | 9.0 |
| Water | ad 100.0 |

The invention claimed is:

1. A cosmetic product, comprising:
a composition A comprising one or more alkalizing agents and one or more direct dyes; and
an aqueous composition B having a pH in a range of 1 to 6 and comprising:
hydrogen peroxide; and
one or more compounds selected from the following groups:

1)

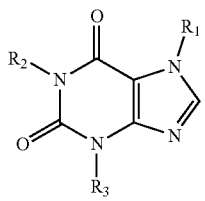

wherein $R_1$, $R_2$, and $R_3$ are independently selected from H and $CH_3$,
2) one or more orthodiphenols or derivative or salt thereof, and
3) one or more imidazolidin-2,4-diones or a derivative or salt thereof.

2. The cosmetic product of claim 1, wherein the one or more direct dyes of the composition A are selected from HC Blue 18, HC Red 18, HC Yellow 16, Disperse Black 9, Acid Yellow 1, 2-amino-6-chloro-4-nitrophenol, and salts thereof.

3. The cosmetic product of claim 1, wherein a total concentration of the one or more direct dyes in the composition A is in a range of 0.001% to 10% by weight, calculated to the total weight of the composition A.

4. The cosmetic product of claim 1, wherein the one or more compounds according to group 1) of the aqueous composition B is selected from caffeine and theobromine.

5. The cosmetic product of claim 1, wherein the one or more orthodiphenols or derivative or salt thereof of the aqueous composition B is selected from the following general structure:

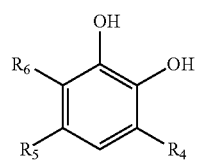

wherein $R_4$, $R_5$, and $R_6$ are independently selected from H, OH, halogen, $C_1$-$C_{12}$ linear or branched alkyl or alkenyl, O—X, $NO_2$, COOH, $SO_3H$, aryl, and heteroaryl, and X is a $C_1$-$C_{12}$ linear or branched alkyl.

6. The cosmetic product of claim 5, wherein $R_4$ is selected from H, OH, halogen $C_1$-$C_{12}$ linear or branched alkyl or alkenyl, O—X, $NO_2$, COOH, $SO_3H$, aryl, and heteroaryl, and $R_5$, and $R_6$ are independently selected from $C_1$-$C_{12}$ linear or branched alkyl or alkenyl, O—X, $NO_2$, COOH, and $SO_3H$.

7. The cosmetic product of claim 1, wherein the one or more orthodiphenols or derivative or salt thereof of the aqueous composition B is selected from the following:

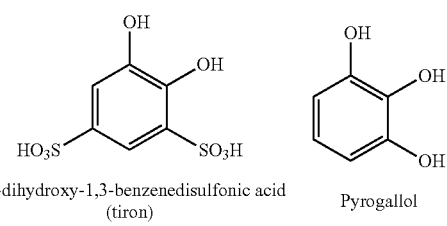

1,4-dihydroxy-1,3-benzenedisulfonic acid (tiron)

Pyrogallol

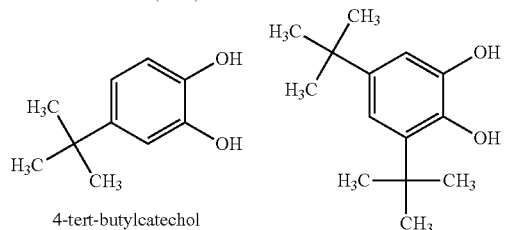

4-tert-butylcatechol 3,5-di-tert-butylcatechol

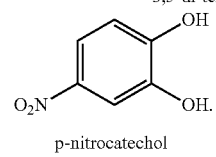

p-nitrocatechol

8. The cosmetic product of claim 1, wherein the one or more imidazolidin-2,4-diones or a derivative or salt thereof of the aqueous composition B has the following general structure:

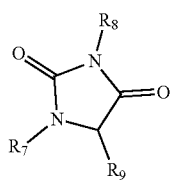

wherein $R_7$, $R_8$ and $R_9$ are independently selected from H, OH, halogen, $C_1$-$C_{12}$ linear or branched alkyl or alkenyl, O—X, COOH, phenyl, diphenyl, and ureyl, and X is a $C_1$-$C_{12}$ linear or branched alkyl.

9. The cosmetic product of claim 1, wherein the one or more imidazolidin-2,4-diones or a derivative or salt thereof of the aqueous composition B is hydantoin or allantoin.

10. The cosmetic product of claim 1, wherein a total concentration of the one or more compounds in the aqueous composition B is in a range of 0.001% to 0.5% by weight, calculated to the total weight of the aqueous composition B.

11. The cosmetic product of claim 1, wherein the composition A or the aqueous composition B further comprises one or more lipophilic compounds.

12. The cosmetic product of claim 1, wherein the composition A or the aqueous composition B further comprises one or more surfactants.

13. A method for dyeing of keratin fibers, comprising:
mixing the composition A and the aqueous composition B of claim 1 to yield a ready-to-use composition having a pH in a range of 7 to 12;
applying the ready-to-use composition onto the keratin fibers;
leaving it for a time period of 1 to 60 min and optionally heating the keratin fibers to a temperature range in a range of 40° C. to 60° C.; and
rinsing off the keratin fibers and optionally shampooing the keratin fibers.

14. A method for improving color intensity and/or wash fastness of direct dyes on keratin fibers comprising:
applying the cosmetic product according to claim 1 to the keratin fibers.

15. The cosmetic product according to claim 1, wherein the one or more alkalizing agents of the composition A is selected from monoethanolamine, diethanolamine, monoethanol methylamine, monoethanol dimethylamine, diethanolmethylamine, monoethanolethylamine, monoethanoldiethylamine, diethanolethylamine, monoethanolpropylamine, monoethanoldipropylamine, diethanolpropylamine, monoethanolbutylamine, diethanolbutylamine, trimethylamine, triethylamine, 2-amino-2-methylpropanol, tris-(hydroxymethyl)-aminomethane, and salts thereof.

16. The cosmetic product according to claim 1, wherein a total concentration of the one or more direct dyes in the composition A is in a range of 0.001% to 1% by weight, calculated to the total weight of the composition A.

17. The cosmetic product according to claim 1, wherein the one or more compounds according to group 1) of the aqueous composition B is caffeine.

18. The cosmetic product according to claim 1, wherein the one or more orthodiphenols or derivative or salt thereof of the aqueous composition B is tiron.

19. The cosmetic product according to claim 1, wherein the one or more imidazolidin-2,4-diones or a derivative or salt thereof of the aqueous composition B is hydantoin.

20. The cosmetic product according to claim 1, wherein the composition A and/or the aqueous composition B further comprise one or more surfactants selected from non-ionic surfactants, anionic surfactants, cationic surfactants, amphoteric/zwitterionic surfactants, and salts thereof.

* * * * *